United States Patent
Choi

(10) Patent No.: US 9,980,797 B2
(45) Date of Patent: May 29, 2018

(54) WATER PRESSURE DRIVEN TOOTH BRUSH

(71) Applicant: Jong-Soo Choi, Seoul (KR)

(72) Inventor: Jong-Soo Choi, Seoul (KR)

(*) Notice: Subject to any disclaimer, the term of this patent is extended or adjusted under 35 U.S.C. 154(b) by 482 days.

(21) Appl. No.: 14/616,101

(22) Filed: Feb. 6, 2015

(65) Prior Publication Data

US 2016/0228226 A1    Aug. 11, 2016

(51) Int. Cl.
   *A61C 17/30*    (2006.01)
   *A61C 17/38*    (2006.01)

(52) U.S. Cl.
   CPC .................................. *A61C 17/38* (2013.01)

(58) Field of Classification Search
   CPC ..... A61C 17/38; A61C 17/30; A61C 17/0214; A46B 13/06
   See application file for complete search history.

(56) References Cited

U.S. PATENT DOCUMENTS

| | | | |
|---|---|---|---|
| 3,909,867 A * | 10/1975 | Hogsell | A61C 17/0214 15/24 |
| 3,927,434 A * | 12/1975 | Burgess | A46B 13/06 15/24 |
| 2004/0045107 A1 | 3/2004 | Egeresi | |
| 2005/0044848 A1 | 3/2005 | Egeresi | |
| 2005/0278878 A1 | 12/2005 | Liao et al. | |

FOREIGN PATENT DOCUMENTS

| | | | |
|---|---|---|---|
| JP | 2000337239 A | 12/2000 | |
| KR | 200374520 Y1 | 1/2005 | |
| KR | 10094845 B1 | 3/2010 | |
| KR | 20130030475 A | 3/2013 | |

* cited by examiner

Primary Examiner — Shay Karls
(74) Attorney, Agent, or Firm — Harness, Dickey & Pierce, P.L.C.

(57) ABSTRACT

A water pressure driven tooth brush according to embodiments includes a hose to be connected to a faucet, a water pressure power generator to generate rotating force by receiving water pressure through the hose, and rotary tooth brush hairs rotated by the water pressure power generator. The water pressure power generator includes a cylindrical housing serving as a tooth brush handle and having a water supply pipe and a water exhaust pipe at a rear portion thereof, and at least one driving shaft at a front portion thereof, a water turbine installed in a rear chamber formed in the cylindrical housing and rotated by pressurized water, and a reduction module installed in a front chamber formed in the cylindrical housing and coupled to a rotating shaft of the water turbine to transfer reduced rotating force to the driving shaft.

13 Claims, 19 Drawing Sheets

WATER PRESSURE DRIVEN TOOTH BRUSH

BACKGROUND

1. Technical Field

Example embodiments relate generally to a water pressure driven tooth brush, and more particularly to a water pressure driven tooth brush which can be connected to a faucet through a hose to rotate tooth brush hairs by hydraulic pressure of running water.

2. Description of the Related Art

Recently, a power tooth brush has been extensively used.

In general, the power tooth brush is classified into a battery exchangeable tooth brush and a battery rechargeable tooth brush.

The battery exchangeable tooth brush needs to exchange the battery, so a user may feel inconvenience. In addition, the battery exchangeable tooth brush may not operate if the battery is not prepared and the battery itself may be discharged in wet environment, such as a bath room, so that a battery receptacle of the battery exchangeable tooth brush may be defected. Meanwhile, the battery rechargeable tooth brush does not need to exchange the battery, but the battery rechargeable tooth brush needs to be connected to a wallet for charging when it is not used, which may cause inconvenience and undesired power consumption.

In addition, studies on a hydraulic tooth brush have been pursued. Korean Patent Registration No. 10-0948945 and U.S. Patent Application Publication No. 2005/0278878 disclose such a hydraulic tooth brush, in which a rotary unit is installed on a tooth brush head to directly rotate tooth brush hairs. However, in the case of the hydraulic tooth brush where the rotary unit is installed on the tooth brush head, the size of the tooth brush head inserted into an oral cavity may be limited. Thus, the size of the rotary unit is also limited, so that sufficient rotating power may not be achieved. For this reason, the rotating operation may be suddenly stopped or the rotating speed may be lowered depending on the contact degree of tooth brush hairs with respect to teeth. In this case, the washing efficiency against the teeth surface may be remarkably lowered.

U.S. Patent Application Publication No. 2004/0045107 discloses a water pressure driven tooth brush, in which a hydraulic rotary unit is installed in a tooth brush handle and rotary tooth brush hairs are rotated by a bevel gear installed in a tooth brush head. However, the tooth brush represents the low power transmission efficiency, so the rotating force may not be sufficiently transferred to the tooth brush hairs, so that the cleaning efficiency for the teeth may be lowered.

SUMMARY

Some example embodiments provide a water pressure driven tooth brush capable of generating great rotating power by forming a vortex flow in a rotating direction of a water turbine.

Some example embodiments provide a water pressure driven tooth brush capable of ensuring the reliable rotating operation of tooth brush hairs by transferring rotating force of a water turbine to the tooth brush hairs through a reduction gear, thereby improving the cleaning efficiency with respect to teeth surfaces.

Some example embodiments provide a water pressure driven tooth brush, which can be configured in a simple structure by minimizing a number of bearing components by simultaneously supporting a water turbine and a reduction gear module using one ring bearing.

According to example embodiments, a water pressure driven tooth brush includes a hose to be connected to a faucet, a water pressure power generator to generate rotating force by receiving water pressure through the hose, and a tooth brush head to rotatably support rotary tooth brush hairs rotated by the water pressure power generator. The water pressure power generator includes a cylindrical housing serving as a tooth brush handle, provided at a rear portion thereof with a water supply pipe connected to the hose and a water exhaust pipe, and provided at a front portion thereof with at least one driving shaft which is rotatably installed and connected to a rotating shaft of the rotary tooth brush hairs, a water turbine installed in a rear chamber formed in the cylindrical housing and rotated by pressurized water supplied into the rear chamber through the water supply pipe, and a reduction module installed in a front chamber formed in the cylindrical housing and coupled to a rotating shaft of the water turbine to transfer reduced rotating force to the at least one driving shaft.

The cylindrical housing may include a rear case provided at a center thereof with the water exhaust pipe, a disc including a water supply pipe eccentrically protruding rearward from a center of a rear surface of the disc and an arc-shape water exhaust port located in opposition to the water supply pipe and communicated with the water exhaust pipe of the rear case, a lower cylindrical case coupled with the disc to form the rear chamber and including a discharge hole communicated with the water supply pipe to discharge the pressurized water to the water turbine, an upper cylindrical case to accommodate a bearing that supports a rotating shaft of the water turbine and the reduction module, and a front case provided at a front surface thereof with at least one protrusion pipe for receiving and supporting the at least one driving shaft and coupled with the upper cylindrical case to form the front chamber.

The lower cylindrical case may be formed in a sidewall thereof with a vertical path communicated with the water supply pipe, and the vertical path is formed at a terminal end thereof with a horizontal path communicated with the discharge hole.

A central line of the horizontal path may be directed to a blade portion spaced apart from the rotating shaft of the water turbine by a predetermined radius.

The lower cylindrical case may be formed in an inner surface of a sidewall thereof with at least one groove to guide a flow of the pressurized water.

The disc may include a front arc-shape elongate hole and a rear arc-shape elongate hole, which are biased from each other by a predetermined angle on a concentric circle, and an arc-shape water exhaust path is disposed to communicate the front arc-shape elongate hole with the rear arc-shape elongate hole.

The disc may include at least one auxiliary water exhaust hole.

The water turbine may include the rotating shaft disposed concentrically with the cylindrical housing, the bearing to support the rotating shaft, a rotary blade extending rearward from a rear end of the rotating shaft, and a driving gear provided at an outer surface of a front portion of the rotating shaft.

The rotary blade may include a plurality of blade plates which are radially disposed while protruding rearward from a rear surface of a flange provided at a rear end of the rotating shaft.

The reduction module may include an internal gear provided at an inner surface of the upper cylindrical case, a rotary disc provided at a front surface thereof with an output shaft, which protrudes forward and is formed at an outer surface thereof with a gear, and provided at a rear surface thereof with a plurality of planet gear shafts arranged around a center of the rotary disc, and a plurality of planet gears coupled with the planet gear shafts, respectively, and engaged between the internal gear and a driving gear of the water turbine.

The water pressure driven tooth brush may further include a water path branching from the water supply pipe and integrally formed with an outer surface of the cylindrical housing, and a spray nozzle provided at a terminal end of the tooth brush head, which rotatably supports the tooth brush hairs, to spray cleaning water supplied through the water path.

According to example embodiments, a water pressure driven tooth brush includes a hose to be connected to a faucet, a tooth brush handle including a water pressure power generator to generate rotating force by receiving water pressure through the hose, and a tooth brush head detachably coupled to an upper end of the tooth brush handle to rotatably support rotary tooth brush hairs rotated by rotating force transferred from the water pressure power generator. The water pressure power generator includes a cylindrical housing serving as the tooth brush handle, provided at a rear portion thereof with a water supply pipe connected to the hose and a water exhaust pipe, and provided at a front portion thereof with at least one driving shaft which is rotatably installed and connected to a rotating shaft of the rotary tooth brush hairs, a water turbine installed in a rear chamber formed in the cylindrical housing and rotated by pressurized water supplied into the rear chamber through the water supply pipe, a reduction module installed in a front chamber formed in the cylindrical housing and coupled to a rotating shaft of the water turbine to transfer reduced rotating force to the at least one driving shaft, and a water path branching from the water supply pipe and integrally formed with an outer surface of the cylindrical housing. The tooth brush head includes a coupling groove formed at a lower end of the tooth brush head and coupled with an upper end of the water path, a spray nozzle provided at a terminal end of the tooth brush head to spray cleaning water supplied through the water path, and a head water path formed between the coupling groove and the spray nozzle.

The water pressure driven tooth brush may further includes a flow rate control valve provided at a middle portion of the water path.

According to example embodiments, a water pressure driven tooth brush includes a hose to be connected to a faucet, a water pressure power generator to generate rotating force by receiving water pressure through the hose, and a tooth brush head to rotatably support rotary tooth brush hairs rotated by the water pressure power generator. The water pressure power generator includes a cylindrical housing serving as a tooth brush handle, provided at a rear portion thereof with a water supply pipe connected to the hose and a water exhaust pipe, and provided at a front portion thereof with at least one driving shaft which is rotatably installed and connected to a rotating shaft of the rotary tooth brush hairs, a water turbine module installed in a rear chamber formed in the cylindrical housing and rotated by pressurized water supplied into the rear chamber through the water supply pipe, and a reduction module installed in a front chamber formed in the cylindrical housing and coupled to a rotating shaft of the water turbine module to transfer reduced rotating force to the at least one driving shaft.

An internal gear may be provided at a boundary between the front chamber and the rear chamber and the internal gear is engaged with the reduction module.

The water turbine module may include a water turbine having a water turbine shaft provided at a front end thereof with a driving shaft gear and at a rear end thereof with a water turbine blade, a water turbine front case formed at a front surface thereof with a shaft hole to rotatably support an upper end of the water turbine shaft of the water turbine and formed in an inner sidewall thereof with a plurality of elongate grooves aligned lengthwise along the water turbine front case, and a water turbine rear case formed at a bottom plate thereof with a support protrusion to rotatably support a lower end of the water turbine shaft and a water exhaust port, formed in an outer sidewall thereof with a plurality of elongate grooves aligned lengthwise along the water turbine rear case, and formed in a sidewall thereof with a through hole communicated with the elongate holes. The elongate grooves of the water turbine rear case may be engaged with the elongate grooves of the water turbine front case as the water turbine rear case is coupled with water turbine front case so that one inlet path or a water exhaust path is formed in the sidewall.

The reduction module may include a rotary disc provided at a front surface thereof with an output shaft, which protrudes forward and is formed at an outer surface thereof with a gear, and provided at a rear surface thereof with a plurality of planet gear shafts arranged around a center of the rotary disc, and a plurality of planet gears coupled with the planet gear shafts, respectively, and engaged between the internal gear and a driving gear of the water turbine.

The tooth brush head may include a pair of rotary tooth brush hairs including a rotating shaft, in which tooth brush hairs are spirally implanted onto an upper portion of the rotating shaft and a lower end of the rotating shaft extends downward, a rotary support member to rotatably support the upper portion of the rotating shaft where the tooth brush hairs of the pair of the rotary tooth brush hairs are spirally implanted, and a head body provided at an upper portion thereof with a coupling protrusion to be coupled with the rotary support member and formed at a lower portion thereof with a shaft hole into which a lower end of the rotating shaft of the pair of the rotary tooth brush hairs is inserted. The rotary support member may include an anti-splash plate to block water splash caused by the pair of the rotary tooth brush hairs.

The water pressure driven tooth brush according to example embodiments can generate high rotating force by rotating the water turbine using hydraulic pressure, and the high rotating force can be reduced through a planet gear when rotating the tooth brush hairs, so that the torque of the tooth brush hairs can be remarkably increased, thereby improving the cleaning efficiency with respect to the teeth surfaces. In addition, since the water turbine and the reduction module can be supported by one ring bearing, a number of bearing components can be minimized, so that the structure of the water pressure driven tooth brush can be simplified.

Effects of the example embodiments may not be limited to the above and other effects, which are not described above, may be fully comprehended to those skilled in the art within the scope of the example embodiments.

BRIEF DESCRIPTION OF THE DRAWINGS

Illustrative, non-limiting example embodiments will be more clearly understood from the following detailed description taken in conjunction with the accompanying drawings.

DETAILED DESCRIPTION OF THE EMBODIMENTS

Figure 1:
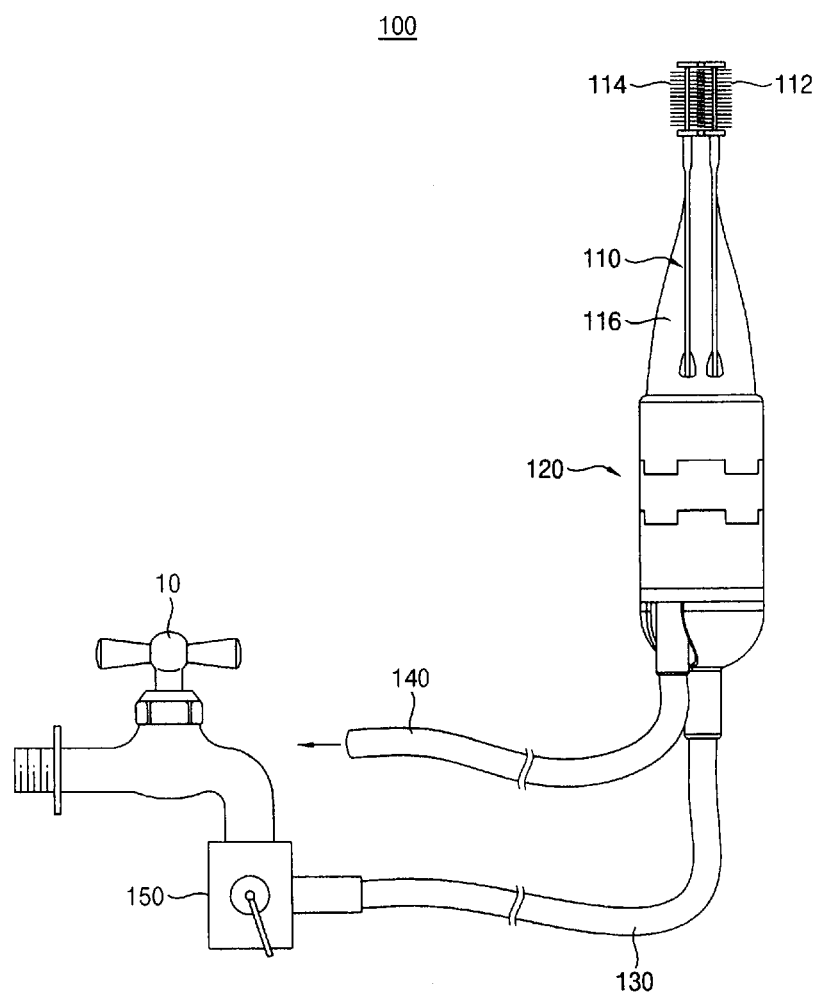
FIG. 1 is a perspective view illustrating an external appearance of a water pressure driven tooth brush according to an example embodiment.

Referring to FIG. 1, a water pressure driven tooth brush 100 includes a tooth brush head 110, a tooth brush handle 120, a water supply hose, a water exhaust hose, and a connection valve 150.

The tooth brush head 110 includes rotary tooth brush hairs 112 and 114 and a head body 116. The tooth brush head 110 may be identical to or similar to a tooth brush head disclosed in Korean Registered Patent No. 10-0683814. Only the tooth brush hairs may be exchangeable in the tooth brush head 110 or the tooth brush head 110 may be exchangeable as a whole. Thus, detailed description of the tooth brush head 110 will be omitted.

The tooth brush handle 120 may sever as a cylindrical housing for a water pressure power generator which will be described later. The tooth brush handle 120 is connected to a faucet 10 through the water supply hose 130 and the connection valve 150, so that pressurized water is supplied to the tooth brush handle 120. In addition, the tooth brush handle 120 may discharge the pressurized water through the water exhaust hose 140.

Figure 2:
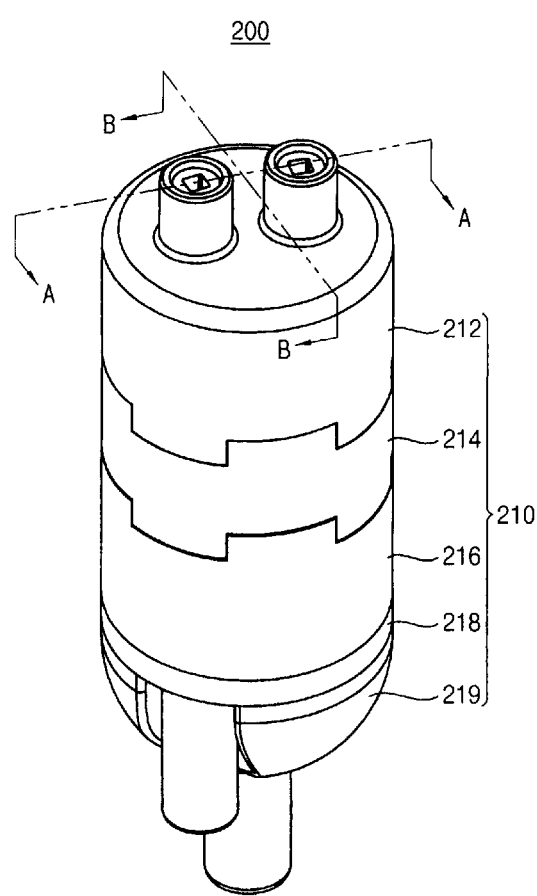
FIG. 2 is a perspective view illustrating an external appearance of a water pressure power generator to generate water pressure power supplied to a tooth brush handle shown in FIG. 1 according to an example embodiment.
Figure 3:
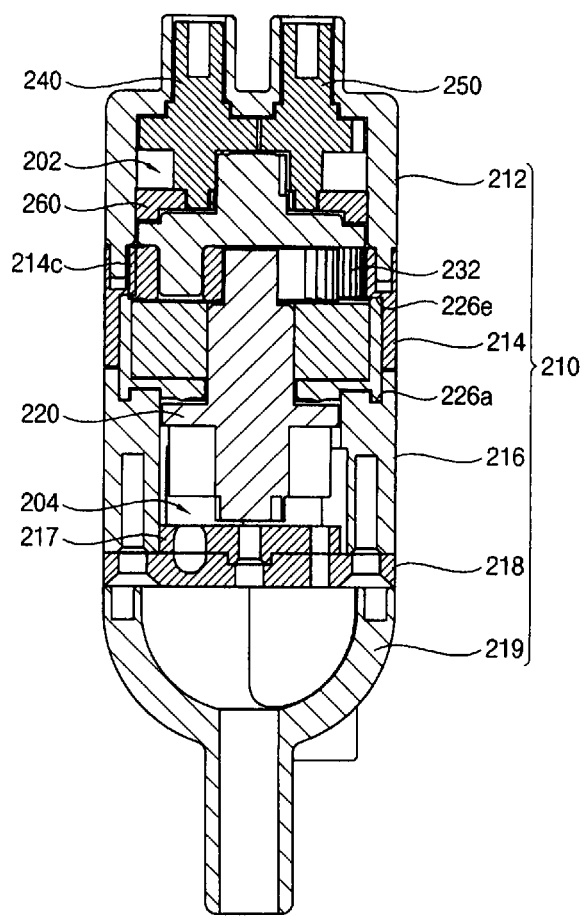
FIG. 3 is a sectional view taken along line A-A of FIG. 2.
Figure 4:
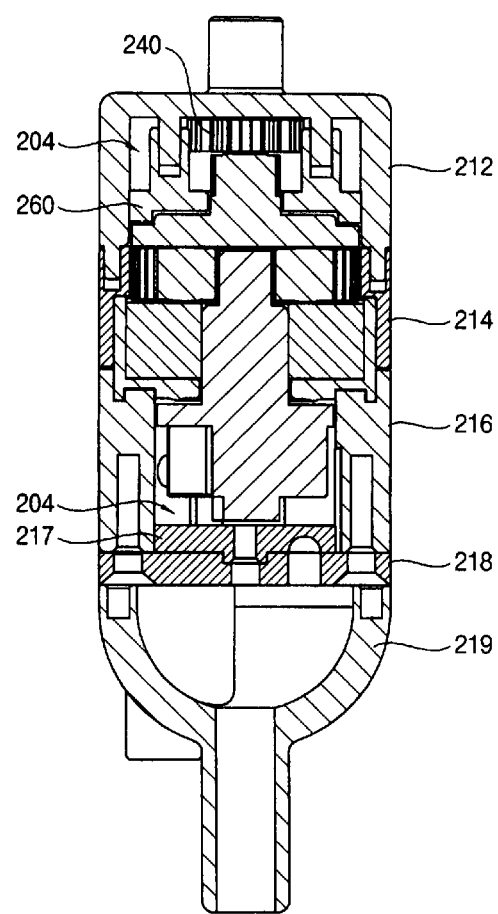
FIG. 4 is a sectional view taken along line B-B of FIG. 2.
Figure 5:
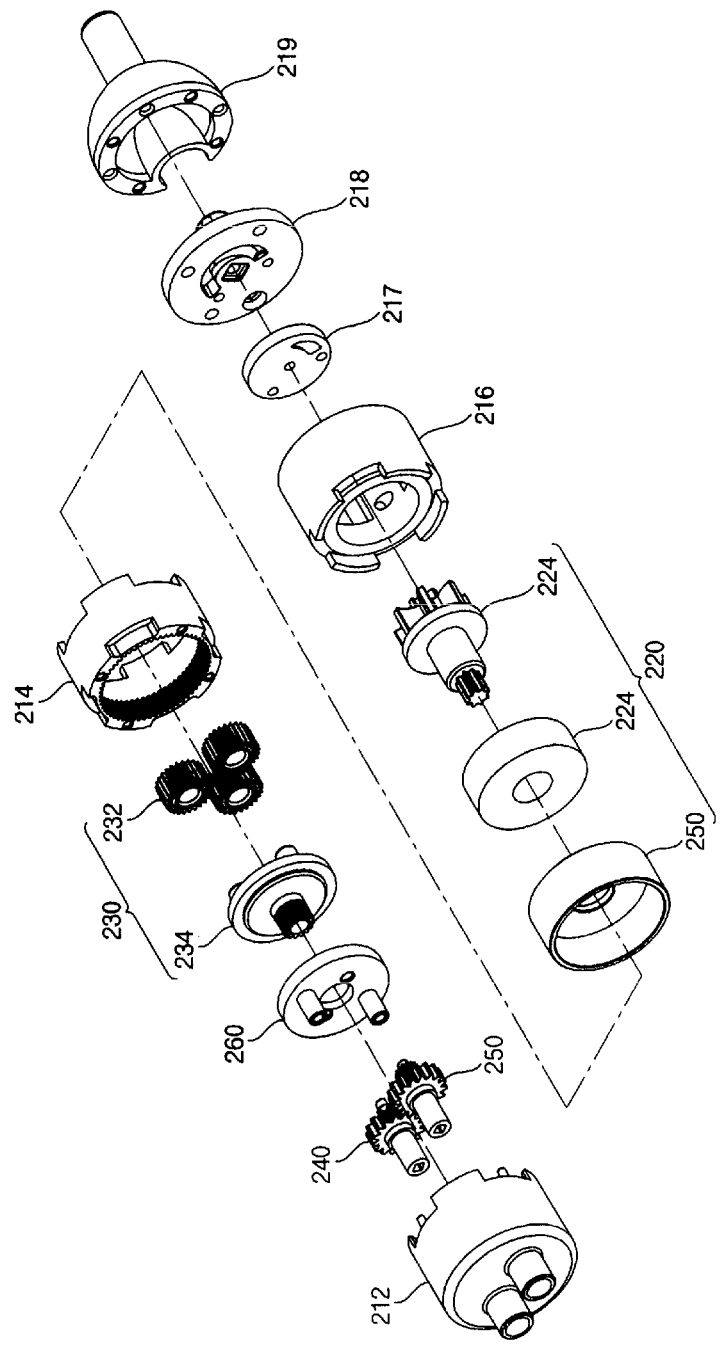
FIG. 5 is an exploded perspective view of FIG. 2.

FIG. 2 is a perspective view illustrating an external appearance of a water pressure power generator 200 to generate water pressure power supplied to the tooth brush handle 120 shown in FIG. 1 according to an example embodiment, FIG. 3 is a sectional view taken along line A-A of FIG. 2, FIG. 4 is a sectional view taken along line B-B of FIG. 2 and FIG. 5 is an exploded perspective view of FIG. 2.

Referring to FIGS. 2 to 5, the water pressure power generator 200 mainly includes a cylindrical housing 210, a water turbine 220, a reduction module 230, two driving shafts 240 and 250, and a support disc 260.

The cylindrical housing 210 may be divided into a front case 212, an upper cylindrical case 214, a lower cylindrical case 216, a disc having first and second discs 217 and 218, and a rear case 219.

The water turbine 220 may include a rotator 222, a bearing 224 and a bearing case 226.

The reduction module 230 may include three planet gears 232 meshed between an internal gear 214f and a driving gear 226 and a rotary disc 234.

Figure 6:
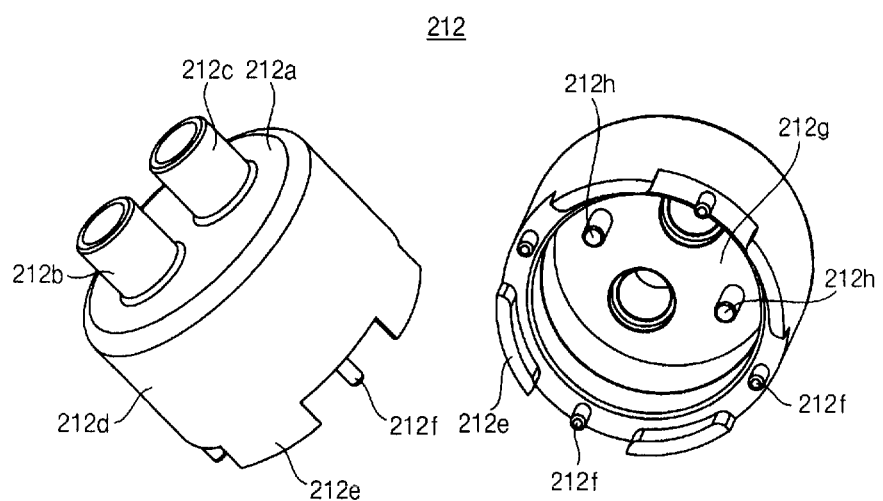
FIG. 6 is a perspective view illustrating an external appearance of a front case shown in FIG. 5.

FIG. 6 is a perspective view illustrating an external appearance of the front case shown in FIG. 5.

Referring to FIG. 6, the front case 212 may have a cylindrical cover shape, in which two protrusion pipes 212b and 212c may protrude forward from a front surface 212a of the front case 212, four coupling plates 212e may be formed at a rear end of a cylindrical sidewall 212d of the front case 212 at a regular interval, and coupling studs 212f may be provided between the coupling plates 212e, respectively. Two coupling bosses 212f may protrude rearward from an inner rear surface 212g of the front case 212.

Figure 7:
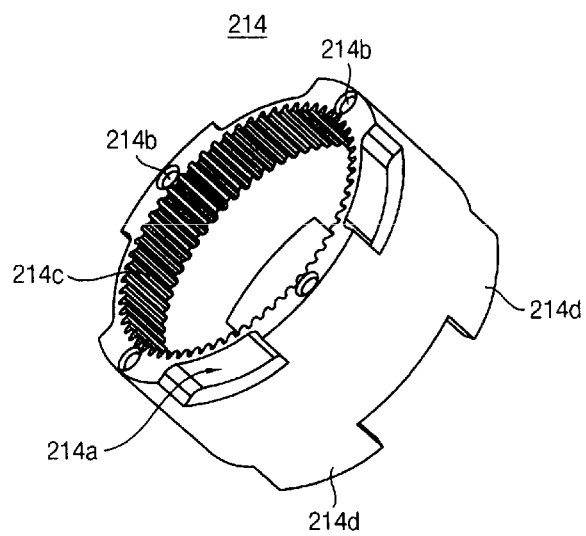
FIG. 7 is a perspective view illustrating an external appearance of an upper cylindrical case shown in FIG. 5.

FIG. 7 is a perspective view illustrating an external appearance of the upper cylindrical case shown in FIG. 5.

Referring to FIG. 7, four coupling recesses 214a may be formed at a front end of the upper cylindrical case 214 and coupling holes 214b may be formed between the coupling recesses 214a, respectively. An internal gear 214c may be provided at an inner surface adjacent to the front end of the upper cylindrical case 214. Four coupling plates 214d may be provided at a rear end of the upper cylindrical case 214 at a regular interval.

The coupling plates 212e of the front case 212 may be engaged with four coupling recesses 214a of the upper cylindrical case 214, and the coupling bosses 212f of the front case 212 may be inserted into the coupling holes 214b of the upper cylindrical case 214, so that the front case 212 may be coupled with the upper cylindrical case 214. An internal space may be formed as the front case 212 is coupled with the upper cylindrical case 214 and the internal space may serve as a front chamber 202. The reduction module 230, the two driving shafts 240 and 250, the support disc 260 and the bearing 224 may be accommodated in the front chamber 202.

Figure 8:
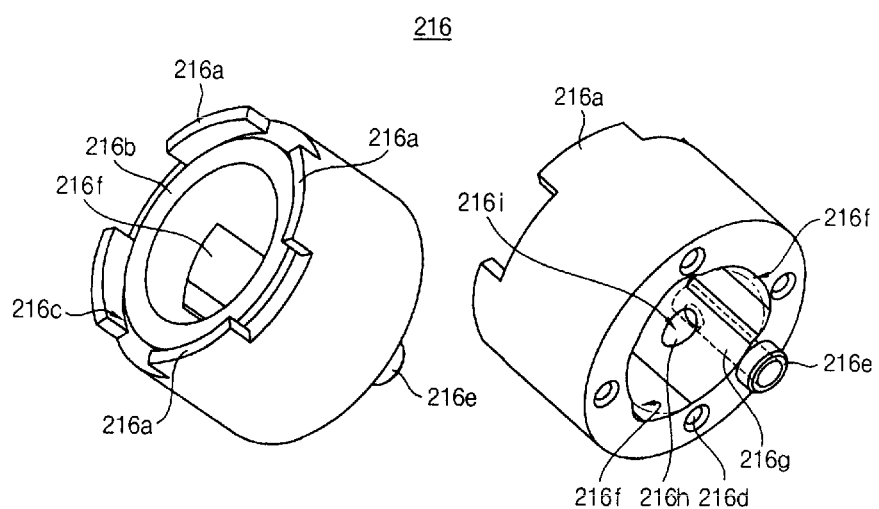
FIG. 8 is a perspective view illustrating an external appearance of a lower cylindrical case shown in FIG. 5.

FIG. 8 is a perspective view illustrating an external appearance of the lower cylindrical case shown in FIG. 5.

Referring to FIG. 8, the lower cylindrical case 216 has a thickness thicker than a thickness of the upper cylindrical case 214. That is, the upper and lower cylindrical cases 214 and 216 may have the same outer diameter, but the inner diameter of the lower cylindrical case 216 is smaller than the inner diameter of the upper cylindrical case 214. Four coupling plates 216a, which protrude forward from an outer edge of the lower cylindrical case 216, may be provided at a front end of the lower cylindrical case 216 and a protrusion ring 216b may protrude forward from an inner edge of the lower cylindrical case 216. Therefore, an insertion slot 216 may be formed between the coupling plates 216a and the protrusion ring 216b. The coupling plates 214d of the upper cylindrical case 214 may be engaged with the coupling plates 216a of the lower cylindrical case 216.

Four coupling holes 216d and one connection pipe 216e may be formed at a rear end of the lower cylindrical case 216. Three grooves 216f may be formed at an inner surface of the lower cylindrical case 216 at a regular interval to induce water pressure flow.

A vertical path 216g, which is communicated with the connection pipe 216e, may be formed in the sidewall of the lower cylindrical case 216 and a horizontal path 216h, which is communicated with a discharge hole 216i, may be formed at a terminal end of the vertical path 216g. The horizontal path 216h may be configured such that the central line of the horizontal path 216h can be directed toward a rotary blade which is remote from a rotating shaft of the water turbine 220 by a predetermined radius.

Figure 9:
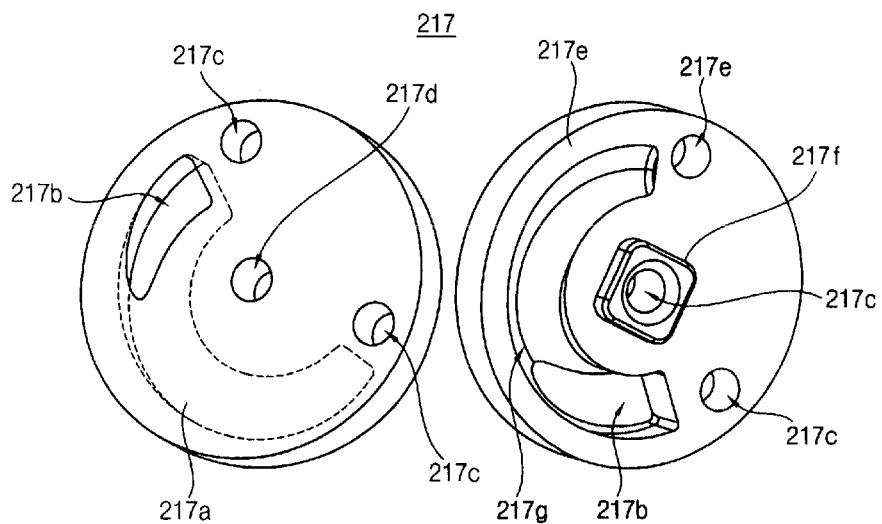
FIG. 9 is a perspective view illustrating an external appearance of a first disc shown in FIG. 5.

FIG. 9 is a perspective view illustrating an external appearance of the first disc shown in FIG. 5.

Referring to FIG. 9, the first disc 217 may have an outer diameter smaller than an inner diameter of the lower cylindrical case 216. An arc-shape elongate hole 217b, two auxiliary water exhaust holes 217c and one coupling hole 217d may be formed at a front surface 217a of the first disc 217. An angular protrusion 217f and an arc-shape groove 217g may be formed at the center of a rear surface 217a of the first disc 217. The two auxiliary water exhaust holes 217c may be disposed at left and right portions about the vertical path 216g, and the arc-shape elongate hole 217b may have one end adjacent to the auxiliary water exhaust hole 217c, which is located in a discharge direction of water discharged from the discharge hole 216i, and the other end spaced apart from the one end while forming an arc in a direction identical to the rotating direction of the water turbine 220. The arc-shape groove 217g formed at the rear surface 217a of the first disc 217 may have one end communicated with the arc-shape elongate hole 217b and extend near to the auxiliary water exhaust hole 217c while forming an arc in a direction identical to the rotating direction of the water turbine 220. One edge of the angular protrusion 217f is directed to the vertical path 216g, so a coupling direction of the first disc 217 coupled with the second disc 218 may be represented. The coupling hole 217d may be formed at the center of the angular protrusion 217f.

Figure 10:
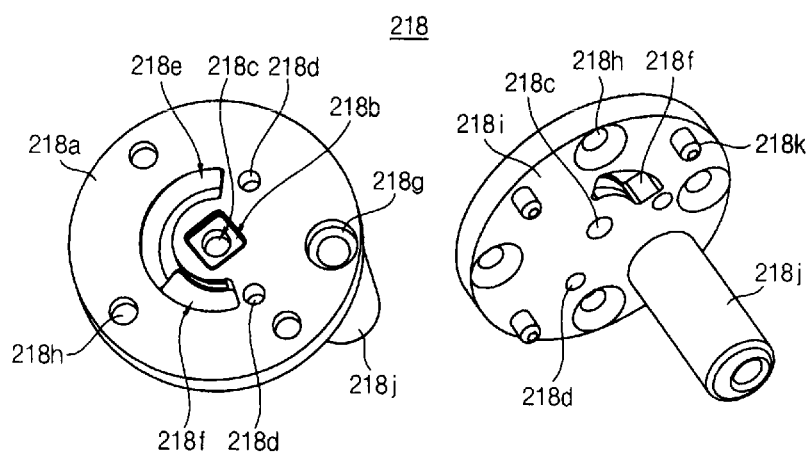
FIG. 10 is a perspective view illustrating an external appearance of a second disc shown in FIG. 5.

FIG. 10 is a perspective view illustrating an external appearance of the second disc shown in FIG. 5.

Referring to FIG. 10, an angular groove 218b, into which the angular protrusion 217f of the first disc 217 is inserted, may be formed at the center of a front surface 218a of the second disc 218 and a coupling hole 218c may be formed at the center of the angular groove 218b. In addition, two auxiliary water exhaust holes 218d, which are communicated with the auxiliary water exhaust holes 217c of the first disc 218, and an arc-shape groove 218e, which faces the arc-shape groove 217g, may be formed at the front surface 218a of the second disc 218. An arc-shape elongate hole 218f may be formed at the other end of the arc-shape groove 218e. Thus, the arc-shape elongate hole 218f may be located in the arc-shape groove 218e in opposition to the arc-shape elongate hole 217b. Therefore, the arc-shape groove 217g may be coupled with the arc-shape groove 218e to form a water exhaust path. That is, the arc-shape elongate hole 217b may serve as an inlet of the water exhaust path and the arc-shape elongate hole 218f may serve as an outlet of the water exhaust path. Therefore, the pressurized water discharged into a rear chamber 204 may be discharged through the main water exhaust path while forming a vortex flow in the rotating direction of the water turbine and maintaining the flow in the rotating direction of the water turbine.

Four coupling holes 218h may be formed at an edge of the front surface 218a at a regular interval and one connection hole 218g may be formed at the edge of the front surface 218a. The connection pipe 216e of the lower cylindrical case 216 may be inserted into the connection hole 218g. One water supply pipe 218j and three coupling bosses 218k may be disposed between four coupling holes 218h at a regular interval in the vicinity of an edge of a rear surface 218i of the second disc 218. The water supply pipe 218j may be communicated with the connection pipe 216e to provide a pressurized water supply path.

Figure 11:
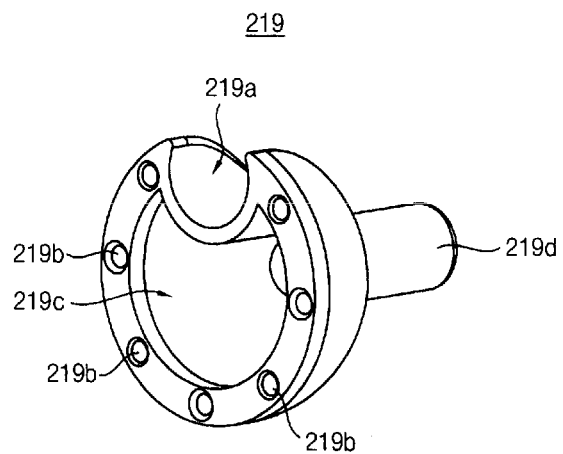
FIG. 11 is a perspective view illustrating an external appearance of a rear case shown in FIG. 5.

FIG. 11 is a perspective view illustrating an external appearance of the rear case shown in FIG. 5.

Referring to FIG. 11, the rear case 219 may be formed at an outer surface thereof with an insertion groove 219a having a semispherical shape. The water supply pipe 218h of the second disc 218 may be inserted into the insertion groove 219a. Seven coupling holes 219b may be regularly formed at an edge of the rear case 219 except for the insertion groove 219a. In addition, a water exhaust pipe 219d may be provided at the center of an outer top surface of the rear case 219 in such a manner that the water exhaust pipe 219d may be communicated with a semispherical inner space. Three coupling bosses 218k may be inserted into three of the seven coupling holes 219b. The water exhaust pipe 219d may protrude rearward from an outer top surface having a semispherical shape.

Therefore, as the lower cylindrical case 216 is coupled with the second disc 218, the rear chamber 204 may be defined therein and the water turbine 220 may be accommodated in the rear chamber 204. Thus, pressurized water may be supplied into the rear chamber 204 by way of water supply pipe 218n—connection pipe 216e—vertical path 216f—horizontal path 216h—discharge hole 216g, thereby rotating the water turbine 220. In addition, the pressurized water supplied into the rear chamber 204 may be exhausted to the outside by way of arc-shape elongate hole 217b—main water exhaust path including arc-shape grooves 217g and 218g—arc-shape elongate hole 218f—semispherical inner space 219c—water exhaust pipe 219d.

The two auxiliary water exhaust holes 218d may allow the rear chamber 204 to communicate with the semispherical inner space 219c such that pressure difference may not occur between the rear chamber 204 and the semispherical inner space 219c.

Since the main water exhaust path is formed in the rotating direction of the water turbine 220, the pumping action may be applied to the water as the water turbine 220 rotates, so the water exhaust efficiency can be improved.

Therefore, if the rear chamber 204 is designed such that the exhaust efficiency of the pressurized water from the rear chamber 204 is higher than the supply efficiency of the pressurized water into the rear chamber 204, the water turbine 220 may always be rotated smoothly in the rear chamber 204, so that great rotating force can be achieved.

Figure 12:
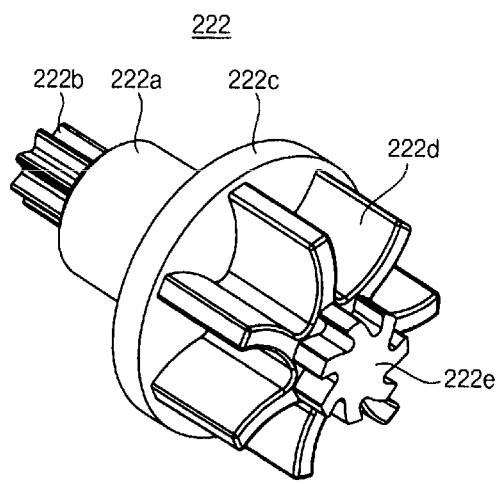
FIG. 12 is a perspective view illustrating an external appearance of a rotator shown in FIG. 5.

FIG. 12 is a perspective view illustrating an external appearance of the rotator shown in FIG. 5.

Referring to FIG. 12, the rotator 222 may include a rotating shaft 222a, a driving gear 222b, a flange 222c, a main rotating blade 222d, and an auxiliary rotating blade 222e. The driving gear 222b may be located in the same position as an internal gear 214c and the rotating shaft 222a may be rotatably supported on the upper cylindrical case 214 by the bearing 224 and the bearing case 226. The main rotating blade 222d may be integrally formed with the flange 222c while protruding rearward from the flange 222c. The main rotating blade 222d may be disposed in the rear chamber 204 to directly receive the pressurized water, which is discharged from the discharge hole, on the blade surface. The auxiliary rotating blade 222e may receive the rotating force from the vortex flow, which is generated as the pressurized water that collides with the main rotating blade 222d is exhausted. The driving gear 222b may serve as an input shaft of the reduction module 230.

Figure 13:
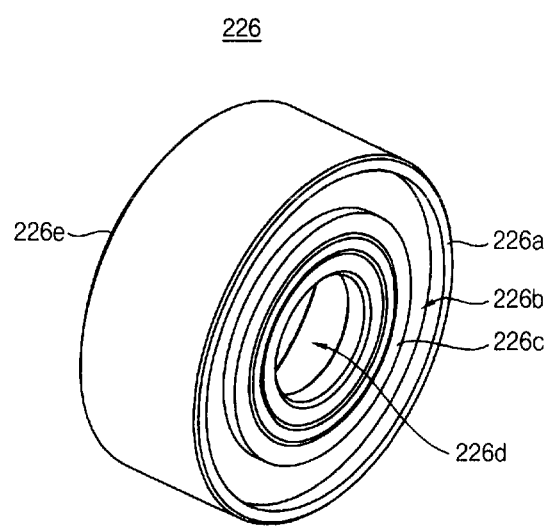
FIG. 13 is a perspective view illustrating an external appearance of a bearing case shown in FIG. 5.

FIG. 13 is a perspective view illustrating an external appearance of the bearing case shown in FIG. 5.

Referring to FIG. 13, a ring groove 226b may be formed inward of a rear end edge 226a of a rear surface of the bearing case 226 and a protrusion ring 226c may be provided around a shaft hole 226d. A front protrusion ring 216b of the lower cylindrical case 216 may be inserted into the ring groove 226b and the rear end edge 226a may be fixedly inserted into an insertion groove 216c. The protrusion ring 226c may minimize a contact of a front surface of the flange 222c of the rotator 222.

Figure 14:
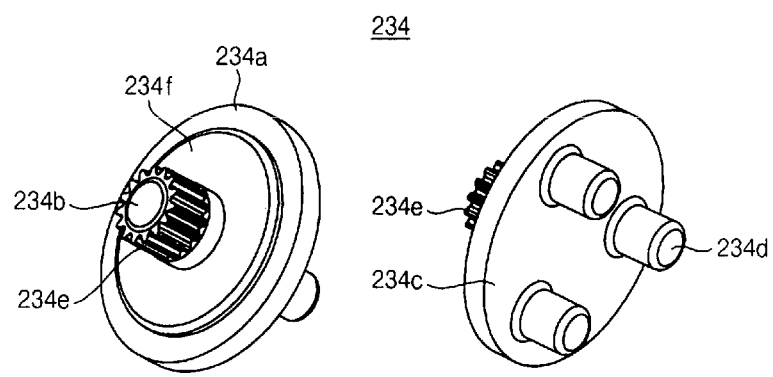
FIG. 14 is a perspective view illustrating an external appearance of a rotary disc shown in FIG. 5.

FIG. 14 is a perspective view illustrating an external appearance of the rotary disc shown in FIG. 5.

Referring to FIG. 14, the rotary disc 234 may include an output shaft 234b protruding from a front surface 234a and three planet gear shafts 234d protruding rearward from a rear surface 234c while being spaced apart from each other at a regular interval. A gear 234e may be formed at an outer surface of the output shaft 234b. Thus, the rotary disc 234 may be supported by the support disc 260 and the internal gear 214f so that the rotary disc 234 may be rotatably installed. A protrusion lubricant surface 234f may be further provided on the front surface 234a of the rotary disc 234. Rear ends of the driving shafts 240 and 250 may come into contact with the protrusion lubricant surface 234f. Rear ends of the three planet gears 234d may come into contact with a front surface of a ring bearing 224.

The driving gear 226 may serve as a sun gear for the three planet gears 234d. Accordingly, the driving gear 226 mat be located at the center of a space corresponding to the internal gear 214c formed at an upper inner portion of the upper cylindrical case 214.

The rotary disc 234 may serve as a carrier to couple the planet gears 232. Thus, the planet gears 232 may revolve around the driving gear 226 while revolving on their own axes.

Figure 15:
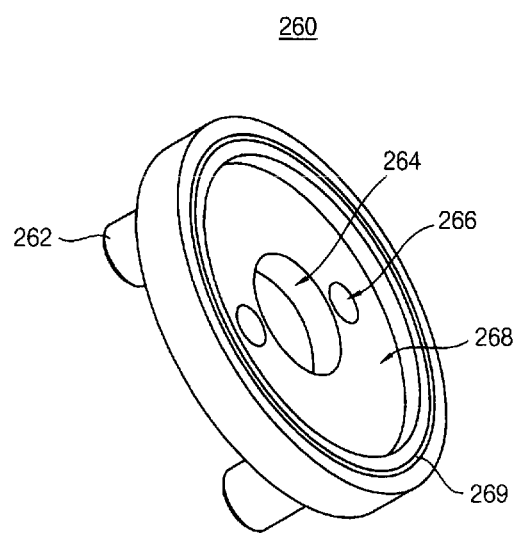
FIG. 15 is a perspective view illustrating an external appearance of a support disc shown in FIG. 5.

FIG. 15 is a perspective view illustrating an external appearance of the support disc shown in FIG. 5.

Referring to FIG. 15, the support disc 260 may include two coupling rods 262 protruding forward from a front surface of the support disc 260, a through hole 264 formed at the center of the support disc 260 and two shaft holes 266 formed around the through hole 264. A recess 268 may be formed at a rear surface of the support disc 260 and a protrusion ring 269 may be formed in the vicinity of an edge of the rear surface of the support disc 260. The protrusion lubricant surface 234f of the rotary disc 234 may be inserted into the recess 268 and the gear 234e of the rotary disc 234 may be inserted through the through hole 264 and protrude toward the front surface of the support disc 260. The protrusion ring 269 may minimize the contact of the front surface of the rotary disc 234.

Figure 16:
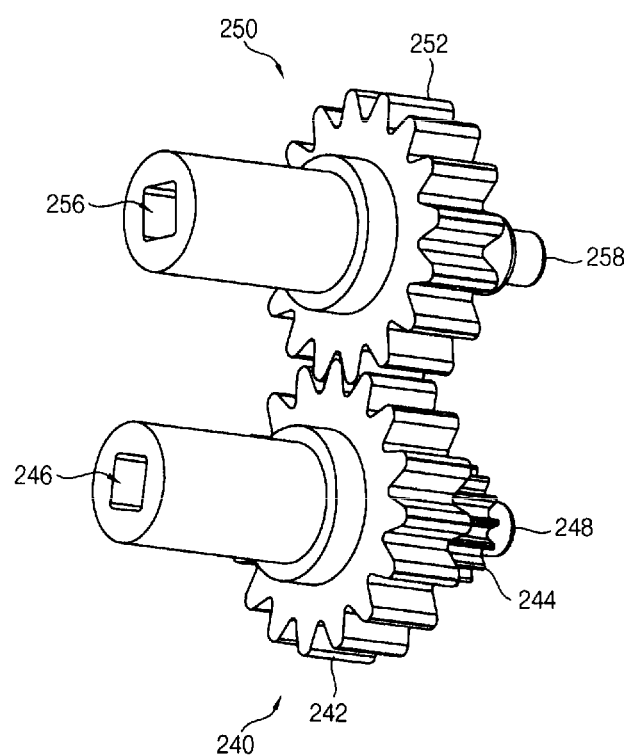
FIG. 16 is a perspective view illustrating an external appearance of a driving shaft shown in FIG. 5.

FIG. 16 is a perspective view illustrating an external appearance of the driving shaft shown in FIG. 5.

Referring to FIG. 16, the driving shafts 240 and 250 may include spur gears 242 and 252 provided at middle portions of the driving shafts 240 and 250, respectively. A gear 244 is provided at a rear outer surface of the spur gear 242. Angular grooves 246 and 256 may be formed at centers of front surfaces of the driving shafts 240 and 250. Front portions of the spur gears 242 and 252 of the driving shafts 240 and 250 may be inserted into protrusion pipes 212b and 212c, respectively, and rear portions 248 and 258 thereof may be rotatably inserted into shaft holes 266 of the support disc 260, respectively.

Since the spur gears 242 and 252 are engaged with each other, the driving shafts 240 and 250 may rotate in opposite directions with respect to each other. Since the gear 244 of the driving shaft 240 is engaged with the gear 234e of the rotary disc 234, the driving shaft 240 may rotate in the opposite direction with respect to the rotating direction of the rotary disc 234 and the driving shaft 250 engaged with the driving shaft 240 through the spur gears may rotate in the rotating direction of the rotary disc 234.

A terminal end of a rotating shaft of tooth brush hairs formed in the tooth brush head may be inserted into the angular grooves 246 and 256 so as to be connected to the driving shafts, respectively.

Therefore, if the water turbine 220 rotates counterclockwise, the rotary disc 230 of the reduction module 230 may rotate counterclockwise. Thus, the driving shaft 240 may receive the rotating force in the clockwise direction, so the driving shaft 250 may rotate counterclockwise.

Left tooth brush hairs connected to the driving shaft 240 may rotate clockwise, and right tooth brush hairs connected to the driving shaft 250 may rotate counterclockwise. Thus, the left and right tooth brush hairs may face each other and clean teeth while sweeping up lateral sides of the teeth from the tooth root in the direction of the tooth surface.

Figure 17:
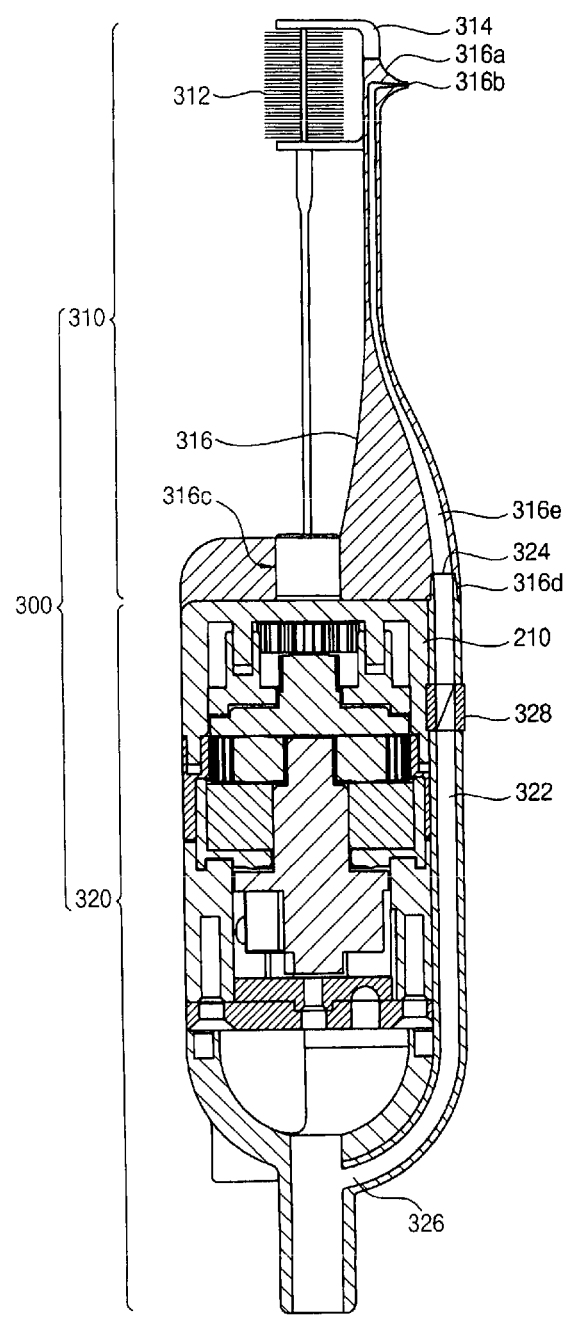
FIG. 17 is a sectional view illustrating a water pressure driven tooth brush according to another example embodiment.

FIG. 17 is a sectional view illustrating a water pressure driven tooth brush according to another example embodiment.

Referring to FIG. 17, the water pressure driven tooth brush 300 according to another example embodiment may include a tooth brush head 310 and a tooth brush handle 320.

The tooth brush head 310 may include tooth brush hairs 312 and a head body 316. The tooth brush hairs 312 are identical to the tooth brush hairs 112 and 114 according to one embodiment described above, so detailed description thereof will be omitted.

The head body 316 may include a spray nozzle 316b provided at a terminal end 316a used to couple a rotary support member 314 of the tooth brush hairs 312. The spray nozzle 316b may protrude to spray washing water in a direction opposite to the tooth brush hairs 312. In another example embodiment, the spray nozzle may be configured to spray washing water toward the spray hairs.

A central coupling hole 316c and a rear coupling hole 316d may be formed at a lower end of the head body 316 in order to couple the tooth brush handle 320. A water path 316e may be formed between the rear coupling hole 316d and the spray nozzle 316b.

The tooth brush handle 320 may include the water pressure power generator 200 according to one embodiment described above. The detailed description about the water pressure power generator will be omitted below. A water path 322 may vertically extend on an outer surface of a cylindrical housing 210 of the water pressure power generator 200. One end of the water path 322 may extend to a coupling protrusion 324 and the other end of the water path 322 may extend to an inlet port 326. The inlet port 326 may be formed inside a water supply pipe of the water pressure power generator 200.

A flow rate control valve 328 may be coupled to a middle portion of the water path 322. The flow rate control valve 328 may rotate about a central axis of the water path 322. The flow rate control valve 328 may have a rotary valve structure where a sectional area for passing the water may be gradually increased as it rotates from one direction, the locking position, to the other direction, the open position. According to another example embodiment, the flow rate control valve 328 may have a vertical slide structure or a horizontal slide structure to adjust the flow rate of water. The flow rate control valve 328 may be a typical flow rate control valve, so detailed description thereof will be omitted.

According to another example embodiment, the tooth brush hairs are rotated by water pressure and water is sprayed into the oral cavity by the spray nozzle, so the tooth brush may be used as an oral cavity cleaning apparatus.

Figure 18:
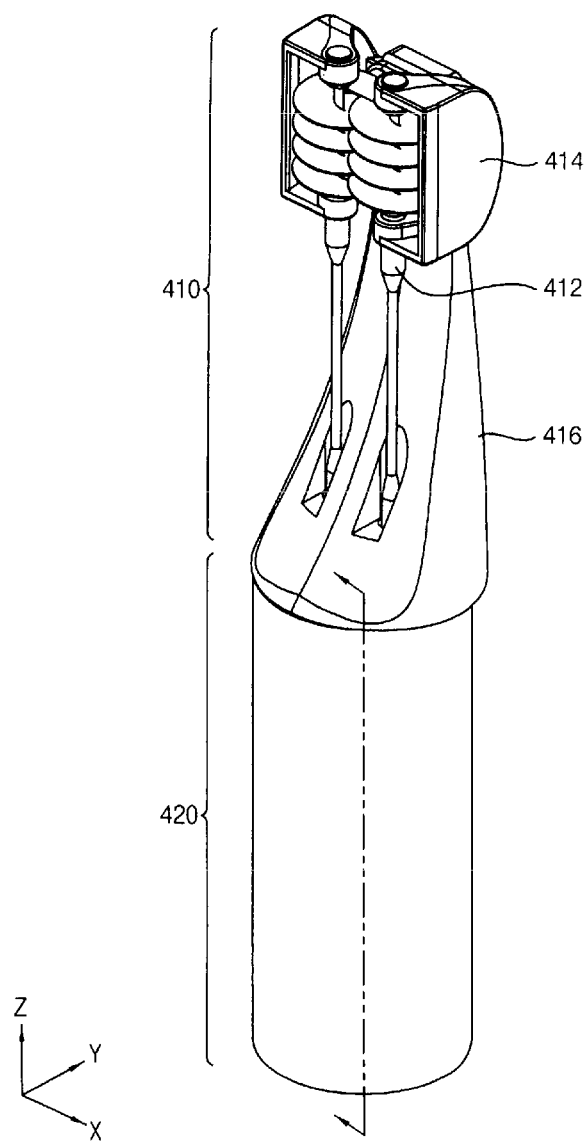
FIG. 18 is a perspective view illustrating an external appearance of a water pressure driven tooth brush according to another example embodiment.

FIG. 18 is a perspective view illustrating an external appearance of a water pressure driven tooth brush according to still another example embodiment.

Referring to FIG. 18, the water pressure driven tooth brush 400 according to still another example embodiment may include a tooth brush head 410 and a tooth brush handle 420. The water pressure driven tooth brush 400 is different from the water pressure driven tooth brush according to one example embodiment described above in that the structure of the tooth brush head 410 is partially modified and some components of a water pressure power generator 500 are modified. Details thereof will be described later.

Figure 19:
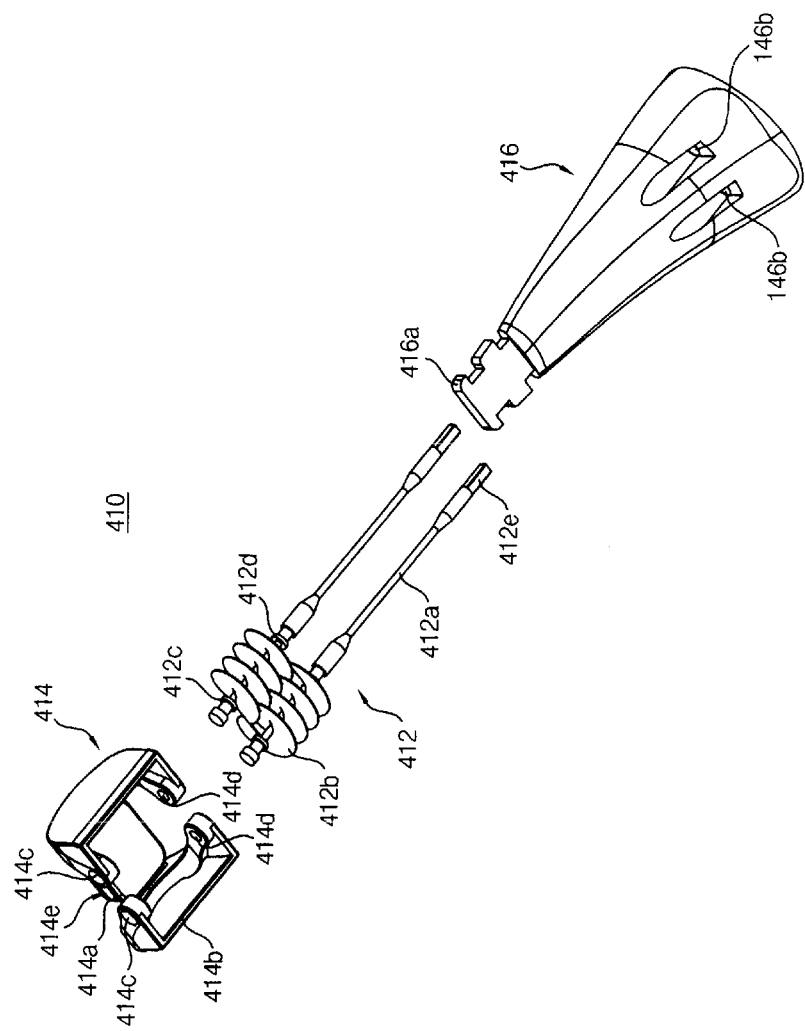
FIG. 19 is an exploded perspective view of a tooth brush head shown in FIG. 18.

FIG. 19 is an exploded perspective view of the tooth brush head 410 shown in FIG. 18.

Referring to FIG. 19, the tooth brush head 410 may include rotary tooth brush hairs 412, a rotary support member 414 and a head body 416.

In the rotary tooth brush hairs 412, tooth brush hairs 412b may be spirally coupled to an upper portion of a rotating shaft 412a. Stoppers 412c and 412d may be provided at upper and lower portions of the rotating shaft 412a, respectively, where the tooth brush hairs 412b are implanted. A shaft coupling part 412e having a square column shape may be provided at a terminal end of the rotating shaft 412a.

The rotary support member 414 may include anti-splash plates 414b protruding in opposition to each other from both sides of a coupling plate 414a and extending forward from a terminal end of the coupling plate 414a. The anti-splash plates 414b may be provided at upper and lower ends thereof with an upper shaft hole 414c and a lower shaft hole 414d, respectively, to support the rotating shaft 412a of the rotary tooth brush hairs 412. A coupling hole 414e may be vertically formed at the center of the coupling plate 414a.

Figure 20:
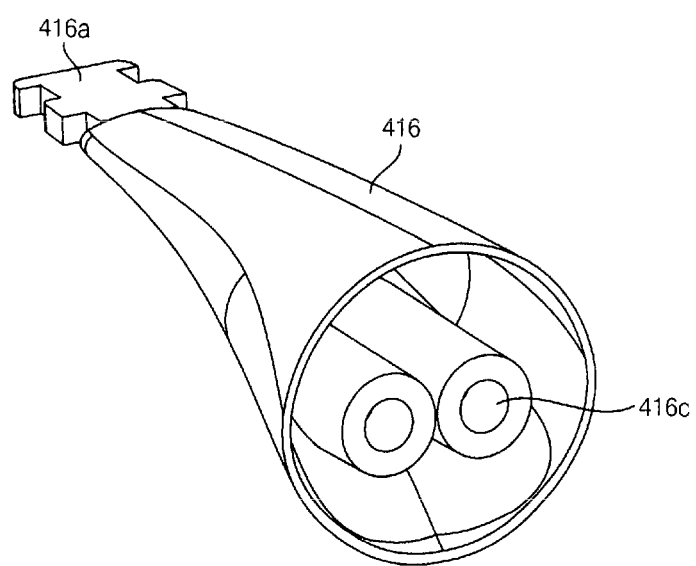
FIG. 20 is a rear perspective view illustrating an external appearance of a head body shown in FIG. 19.

The head body 416 may have a shape which is asymmetrically tapered and an upper end portion is biased from a central line such that the rotating shaft 412a can be aligned on the central vertical line. A coupling protrusion 416a, which is inserted into the coupling hole 414d of the coupling plate 414a, may be provided at an upper end of the head body 416. The coupling protrusion 416a may have a concavo-convex structure to mesh with a concavo-convex structure formed in the coupling hole 414d. The concavo-convex structures are press-fitted with each other, so the tight coupling can be achieved. A pair of shaft insertion grooves 416b may be formed at the center of a lower end of the head body 416 and the rotating shafts 412a may be inserted into the shaft insertion grooves 416b. As shown in FIG. 20, a pair of cylinders 416c, which define the pair of shaft insertion grooves 416b, may extend downward from a bottoms surface of the head body 416. Lower ends of the pair of cylinders 416c may extend until they reach the lower end of the head body 416.

The rotary tooth brush hairs 412 may sequentially pass through a lower end of the rotating shaft 412a, the upper shaft hole 414c of the anti-splash plate 414b and the lower shaft hole 414d of the anti-splash plate 414b. The upper stopper 412c of the rotary tooth brush hairs 412 may come into contact with a lower end of the upper shaft hole 414c and the lower stopper 412d of the rotary tooth brush hairs 412 may come into contact with an upper end of the lower shaft hole 414d, so that the tooth brush hairs 412b may be located in a space between the upper shaft hole 414c and the lower shaft hole 414d. Thus, the water splash scattered to the outside due to the rotation of the tooth brush hairs 412b can be blocked by the anti-splash plate 414b.

Figure 21:
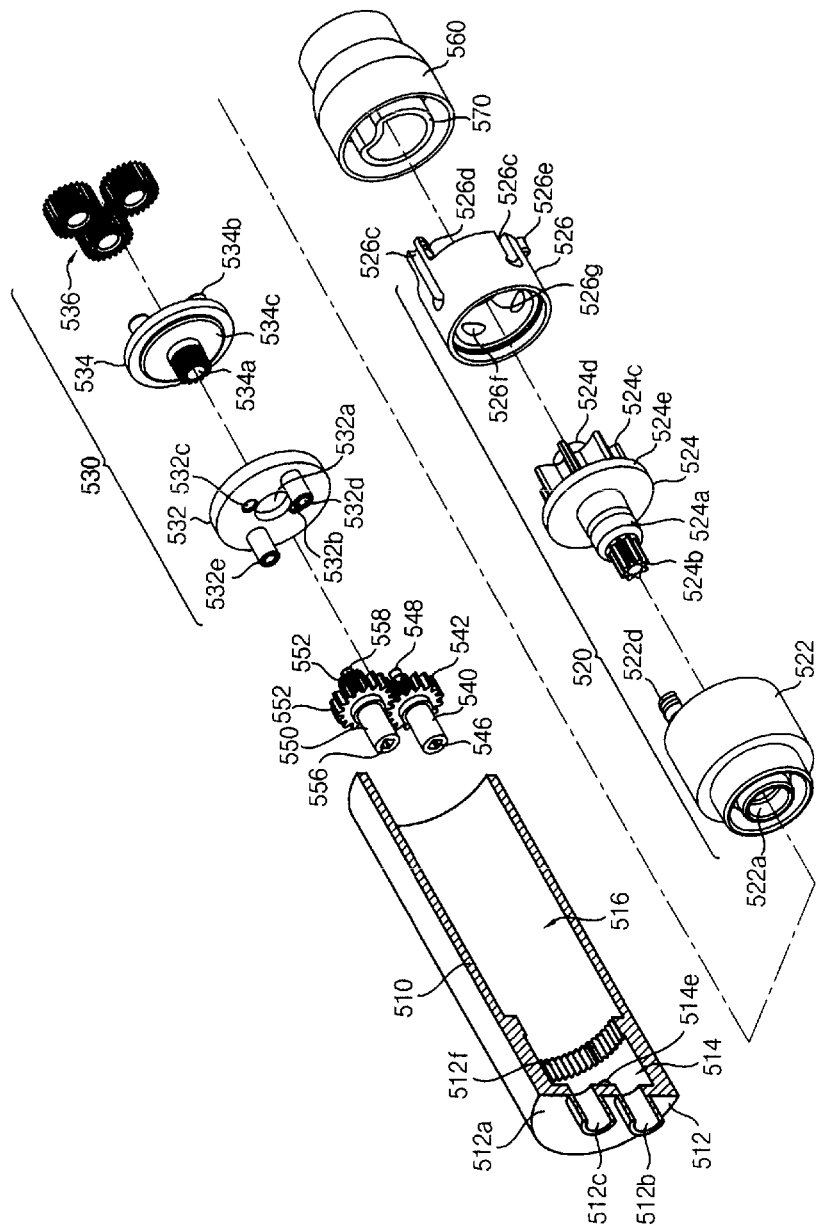
FIG. 21 is an exploded perspective view illustrating a water pressure power generator to generate water pressure power supplied to a tooth brush handle shown in FIG. 18 according to an example embodiment.
Figure 22:
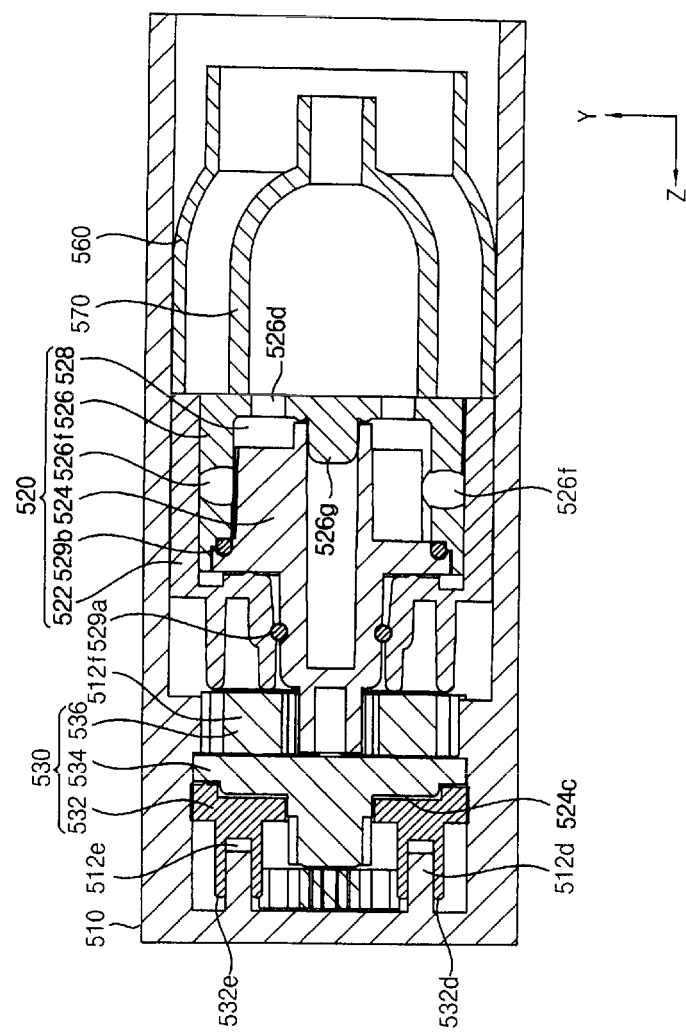
FIG. 22 is a sectional view of a water pressure power generator taken along plane Z-Y of FIG. 18.
Figure 23:
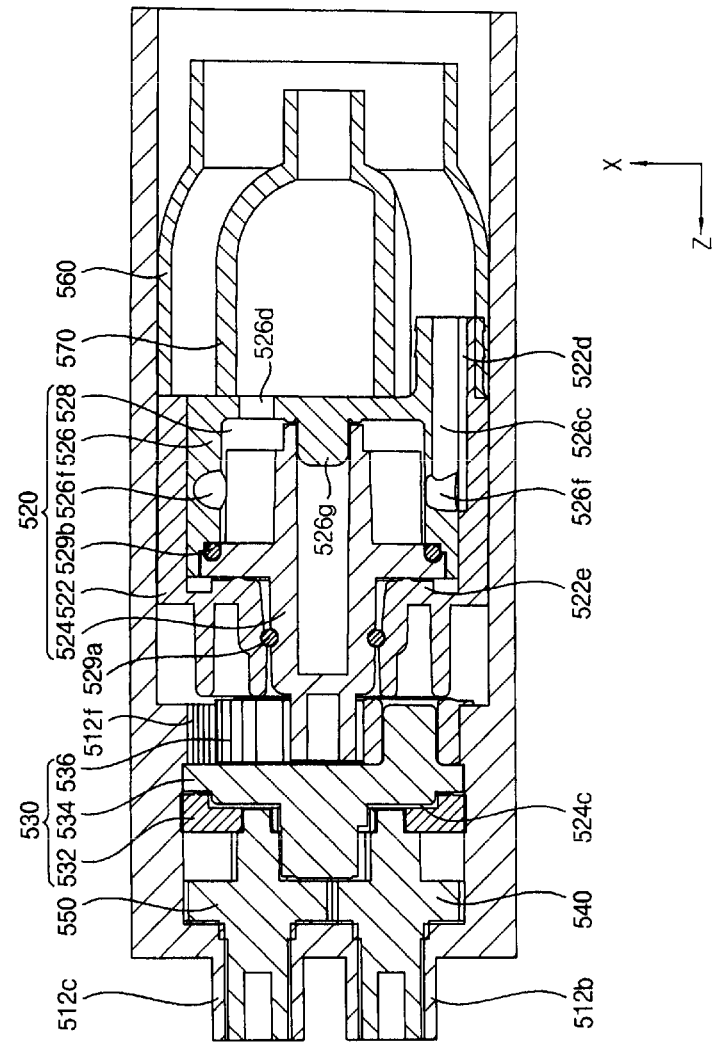
FIG. 23 is a sectional view of a water pressure power generator taken along plane Z-X of FIG. 18.

FIG. 21 is an exploded perspective view illustrating the water pressure power generator 500 to generate water pressure power supplied to the tooth brush handle 420 shown in FIG. 18 according to an example embodiment. FIG. 22 is a sectional view of the water pressure power generator 500 taken along plane Z-Y of FIG. 18. FIG. 23 is a sectional view of the water pressure power generator 500 taken along plane Z-X of FIG. 18.

Referring to FIGS. 21 to 23, the water pressure power generator 500 mainly includes a cylindrical housing 510, a water turbine module 520, a reduction module 530, two driving shafts 540 and 550, a rear outer container 560 and a rear inner container 570.

A rear portion of the cylindrical housing 510 may be open and a front portion of the cylindrical housing 510 may be blocked by a front plate 512. An inside of the cylindrical housing 510 may be divided into a front chamber 514 and a rear chamber 516. Two coupling pipes 512b and 512c may protrude forward from an outer surface 512a of the front plate 512. The two coupling pipes 512b and 512c may be spaced to the left and right from the central line at the same distance. The two coupling pipes 512b and 512c may be inserted into a pair of cylinders 416c. A pair of rear protrusions 512d and 512e, which are spaced up and down from the central line at the same distance, may be provided at an inner surface of the front plate 512. An internal gear 512f may be provided at a border between the front chamber 514 and the rear chamber 516 of the cylindrical housing 510.

The two driving shafts 540 and 550 and the reduction module 530 may be accommodated in the front chamber 514 of the cylindrical housing 510 and the water turbine module 520, the rear outer container 560 and the rear inner container 570 may be accommodated in the rear chamber 516.

The reduction module 530 may include a support disc 532, a rotary disc 534 and three planet gears 536. The support disc 532 may have a central through hole 532a formed at the center of the support disc 532 and two shaft holes 532b and 532c spaced to the left and right about the central through hole 532a, respectively. In addition, the support disc 532 may be provided at the front surface thereof with two coupling pipes 532d and 532e spaced up and down at the same distance from the central through hole 532a, respectively.

The rotary disc 534 may include an output shaft gear 534a protruding from a front surface of the rotary disc 534 and three planet gear shafts 534b protruding rearward from a rear sauce of the rotary disc 534 while being spaced apart from each other at a regular interval. Thus, the rotary disc 534 may be rotatably installed while being supported by the support disc 532 and the internal gear 512f. A protrusion lubricant surface 534c may be further provided at the front surface of the rotary disc 534. Rear ends of the driving shafts 540 and 550 may come into contact with the protrusion lubricant surface 534c.

The rotary disc 534 may serve as a carrier to couple the planet gears 536. Thus, the planet gears 536 may revolve around the driving gear, which will be described later, while revolving on their own axes.

The driving shafts 540 and 550 may include spur gears 542 and 552 provided at middle portions of the driving shafts 540 and 550, respectively. A gear 554 is provided at a rear outer surface of the spur gear 542. Angular grooves 546 and 556 may be formed at centers of front surfaces of the driving shafts 540 and 550. Front portions of the spur gears 542 and 552 of the driving shafts 540 and 550 may be inserted into coupling pipes 512b and 512c, respectively, rear portions 548 and 558 thereof may be rotatably inserted into shaft holes 532b and 532c of the support disc 532, respectively.

Since the spur gears 542 and 552 are engaged with each other, the driving shafts 540 and 550 may rotate in opposite directions with respect to each other. Since the gear 554 of the driving shaft 550 is engaged with the output shaft gear 534a of the rotary disc 534, the driving shaft 550 may rotate in the opposite direction with respect to the rotating direction of the rotary disc 534 and the driving shaft 540 engaged with the driving shaft 550 through the spur gears may rotate in the rotating direction of the rotary disc 534.

A terminal end 412a of a rotating shaft of tooth brush hairs formed in the tooth brush head 410 may be inserted into the angular grooves 546 and 556 so as to be connected to the driving shafts 540 and 550, respectively.

Therefore, if the water turbine module 520 rotates counterclockwise, the rotary disc 534 of the reduction module 530 may rotate counterclockwise. Thus, the driving shaft 550 may receive the rotating force in the clockwise direction, so the driving shaft 540 may rotate counterclockwise.

Right tooth brush hairs connected to the driving shaft 550 may rotate clockwise, and left tooth brush hairs connected to the driving shaft 540 may rotate counterclockwise. Thus, the left and right tooth brush hairs may face each other and clean teeth while sweeping up lateral sides of the teeth from the tooth root in the direction of the tooth surface.

The water turbine module 520 may include a water turbine front case 522, a water turbine 524 and a water turbine rear case 526.

The water turbine front case 522 may be coupled with the water turbine rear case 526 to form a water turbine chamber 528 therein and the water turbine 524 may be rotatably installed in the water turbine chamber 528.

A driving shaft gear 524b may be provided at a front end of a water turbine shaft 524a of the water turbine 524 and water turbine blades 524c may be provided at a rear end of the water turbine shaft 524a of the water turbine 524. The water turbine blades 524c may be integrally formed with a rear surface of a flange 524e. A shaft groove 524b may be formed at a terminal end of the water turbine 524.

The water turbine front case 522 may be prepared in the form of a cylinder in which a front portion of the cylinder is closed and a rear portion of the cylinder is open. A bearing 522a having a dual structure of an inner container and an outer container may protrude forward from a front surface of the water turbine front case 522. The bearing 522a may support bottom surfaces of the three planet gears by using terminal ends of the inner container and the outer container to support the revolution and rotation of the planet gears.

Figure 24:
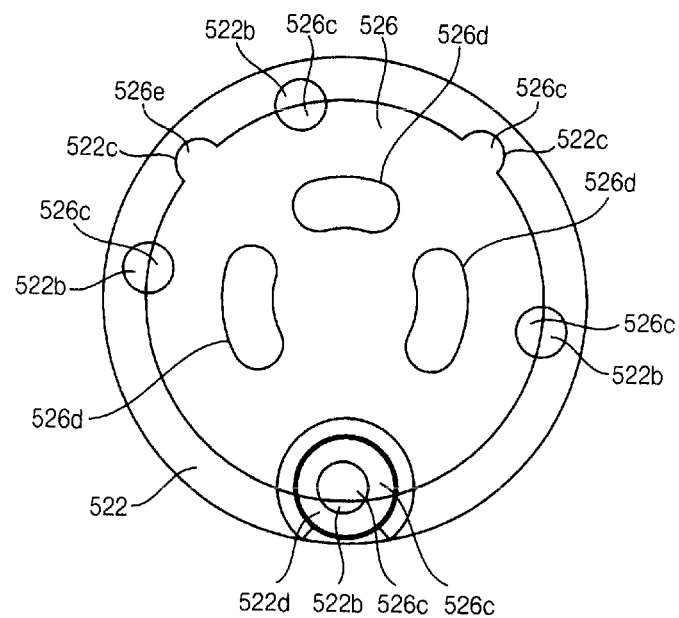
FIG. 24 is a bottom view of a water turbine module shown in FIG. 21.

FIG. 24 is a bottom view of the water turbine module 520 shown in FIG. 21.

Referring to FIG. 24, four long grooves 522b, which extend lengthwise from a lower end of the water turbine front case 522, and two short align grooves 522c may be formed at an inner surface of a sidewall of the water turbine front case 522. A protrusion 522d may extend rearward from a lower end of the sidewall of the water turbine front case 522. A groove may be formed at an inner surface of the protrusion 522d to communicate with one of the four long grooves 522b. An annular rim 522e may be formed at a rear surface of the four circular grooves 522b, which adheres to the flange 524e, to rotatably support the water turbine 524.

The water turbine rear case 526 may be prepared in the form of a cylinder in which a front portion of the cylinder is open and a rear portion of the cylinder is closed. Three water exhaust holes 526b may be formed in a bottom plate 526a of the water turbine rear case 526. Four long grooves 526c, which extend lengthwise from a lower end of the water turbine rear case 526 by a predetermined height, and two align protrusions 526e may be formed at a lower end of a sidewall of the water turbine rear case 526. A protrusion 526d may extend rearward from a lower end of the sidewall of the water turbine rear case 526. A groove may be formed at an inner surface of the protrusion 526d to communicate with one of the four long grooves 526c. Through holes 526f may be formed at upper ends of the four long grooves 526c, respectively, to communicate with the water turbine chamber 528. The through holes 526f may be oblique by a predetermined angle with respect to a virtual line directed to the water turbine axis in such a manner that the through holes 526f can be directed to the water turbine blades 524c installed in the water turbine chamber 528. A water turbine shaft support protrusion 526g may protrude forward from the center of the bottom plate 526a of the water turbine rear case 526.

Therefore, if the water turbine front case 522 is coupled with the water turbine rear case 526 by allowing the two align short grooves 522c of the water turbine front case 522 to engage with the two align protrusions 526c of the water turbine rear case 526, the water turbine chamber 528 may be formed inside the water turbine front case 522 and the water turbine rear case 526 and four vertical paths may be formed between adjacent sidewalls of the water turbine front case 522 and the water turbine rear case 526. In addition, the protrusion 522d of the water turbine front case 522 may be coupled with the protrusion 526d of the water turbine rear case 526 to form one inlet pipe. The inlet pipe may be communicated with one of the four vertical paths to supply pressurized water into the water turbine chamber 528.

The water turbine 524 may be rotatably installed between the bearing 522a and the support protrusion 526g in the water turbine chamber 528. The driving shaft gear 524b of the water turbine 524 may be located at the same height as the internal gear 522a and the water turbine shaft 524a may be rotatably supported in the shaft hole of the bearing 522a of the water turbine front case 522 by interposing an O-ring 524a therebetween. The water turbine blades 524c may be integrally formed with the flange 524e while protruding rearward from the flange 524e. The water turbine blades 524c may be disposed in the water turbine chamber 528 to directly receive the pressurized water, which is discharged from the through holes 526f, on the blade surface. The driving shaft gear 524b may serve as an input shaft of the reduction module 530. An O-ring 529b may be installed between a lower end edge of the flange 524e of the water turbine 524 and an upper end edge of the water turbine rear case 526. Thus, two O-rings 529a and 529b may prevent the pressurized water from leaking to the reduction module 530 while maintaining the rotation state.

The rear outer container 560 may have an outer diameter equal to an outer diameter of the water turbine front case 522 and the rear inner container 570 may have an inner diameter similar to an inner diameter of the water turbine rear case 526. Thus, the rear inner container 570 may be communicated with three water exhaust ports of the water turbine rear case 526 to form the main water exhaust path. The rear outer container 560 may be communicated with three of the four vertical paths except for the vertical path that forms the inlet pipe. Thus, the pressurized water introduced into the water turbine chamber 528 may be rapidly exhausted through the main water exhaust path as well as the auxiliary water exhaust path. Since the pressurized water can be rapidly exhausted from the water turbine chamber 528, the pressurized water may not interfere with the rotation of the water turbine blades.

Although the disclosure has been described with reference to some example embodiments, it will be understood that those skilled in the art may make certain changes and modifications within the spirit of the disclosure and scope of the appended claims.

What is claimed is:

1. A water pressure driven tooth brush comprising:
a hose to be connected to a faucet;
a water pressure power generator to generate rotating force by receiving water pressure through the hose; and
a tooth brush head to rotatably support rotary tooth brush hairs rotated by the water pressure power generator,
wherein the water pressure power generator includes:
a cylindrical housing serving as a tooth brush handle, provided at a rear portion thereof with a water supply pipe connected to the hose and a water exhaust pipe, and provided at a front portion thereof with at least one driving shaft which is rotatably installed and connected to a rotating shaft of the rotary tooth brush hairs;
a water turbine installed in a rear chamber formed in the cylindrical housing and rotated by pressurized water supplied into the rear chamber through the water supply pipe; and
a reduction module installed in a front chamber formed in the cylindrical housing and coupled to a rotating shaft of the water turbine to transfer reduced rotating force to the at least one driving shaft; and
wherein the cylindrical housing includes:
a rear case provided at a center thereof with the water exhaust pipe;
a disc including a water supply pipe eccentrically protruding rearward from a center of a rear surface of the disc and an arc-shape water exhaust port located in opposition to the water supply pipe and communicated with the water exhaust pipe of the rear case;
a lower cylindrical case coupled with the disc to form the rear chamber and including a discharge hole communicated with the water supply pipe to discharge the pressurized water to the water turbine;
an upper cylindrical case to accommodate a bearing that supports a rotating shaft of the water turbine and the reduction module; and
a front case provided at a front surface thereof with at least one protrusion pipe for receiving and supporting the at least one driving shaft and coupled with the upper cylindrical case to form the front chamber.

2. The water pressure driven tooth brush of claim 1, wherein the lower cylindrical case is formed in a sidewall thereof with a vertical path communicated with the water supply pipe, and the vertical path is formed at a terminal end thereof with a horizontal path communicated with the discharge hole.

3. The water pressure driven tooth brush of claim 2, wherein a central line of the horizontal path is directed to a blade portion spaced apart from the rotating shaft of the water turbine by a predetermined radius.

4. The water pressure driven tooth brush of claim 1, wherein the lower cylindrical case is formed in an inner surface of a sidewall thereof with at least one groove to guide a flow of the pressurized water.

5. The water pressure driven tooth brush of claim 1, wherein the disc includes a front arc-shape elongate hole and a rear arc-shape elongate hole, which are biased from each other by a predetermined angle on a concentric circle, and an arc-shape water exhaust path is disposed to communicate the front arc-shape elongate hole with the rear arc-shape elongate hole.

6. The water pressure driven tooth brush of claim 5, wherein the disc includes at least one auxiliary water exhaust hole.

7. The water pressure driven tooth brush of claim 1, wherein the water turbine comprises:
the rotating shaft disposed concentrically with the cylindrical housing;
the bearing to support the rotating shaft;
a rotary blade extending rearward from a rear end of the rotating shaft; and
a driving gear provided at an outer surface of a front portion of the rotating shaft.

8. The water pressure driven tooth brush of claim 7, wherein the rotary blade includes a plurality of blade plates which are radially disposed while protruding rearward from a rear surface of a flange provided at a rear end of the rotating shaft.

9. The water pressure driven tooth brush of claim 1, wherein the reduction module comprises:
an internal gear provided at an inner surface of the upper cylindrical case;
a rotary disc provided at a front surface thereof with an output shaft, which protrudes forward and is formed at an outer surface thereof with a gear, and provided at a rear surface thereof with a plurality of planet gear shafts arranged around a center of the rotary disc; and
a plurality of planet gears coupled with the planet gear shafts, respectively, and engaged between the internal gear and a driving gear of the water turbine.

10. The water pressure driven tooth brush of claim 1, further comprising:
a water path branching from the water supply pipe and integrally formed with an outer surface of the cylindrical housing; and
a spray nozzle provided at a terminal end of the tooth brush head, which rotatably supports the tooth brush hairs, to spray cleaning water supplied through the water path.

11. A water pressure driven tooth brush comprising:
a hose to be connected to a faucet;
a water pressure power generator to generate rotating force by receiving water pressure through the hose; and
a tooth brush head to rotatably support rotary tooth brush hairs rotated by the water pressure power generator,
wherein the water pressure power generator comprises:
a cylindrical housing serving as a tooth brush handle, provided at a rear portion thereof with a water supply pipe connected to the hose and a water exhaust pipe, and provided at a front portion thereof with at least one driving shaft which is rotatably installed and connected to a rotating shaft of the rotary tooth brush hairs;
a water turbine module installed in a rear chamber formed in the cylindrical housing and rotated by pressurized water supplied into the rear chamber through the water supply pipe; and
a reduction module installed in a front chamber formed in the cylindrical housing and coupled to a rotating shaft of the water turbine module to transfer reduced rotating force to the at least one driving shaft;
wherein an internal gear is provided at a boundary between the front chamber and the rear chamber and the internal gear is engaged with the reduction module; and
wherein the water turbine module includes:
a water turbine having a water turbine shaft provided at a front end thereof with a driving shaft gear and at a rear end thereof with a water turbine blade;
a water turbine front case formed at a front surface thereof with a shaft hole to rotatably support an upper end of the water turbine shaft of the water turbine and formed in an inner sidewall thereof with a plurality of elongate grooves aligned lengthwise along the water turbine front case; and
a water turbine rear case formed at a bottom plate thereof with a support protrusion to rotatably support a lower end of the water turbine shaft and a water exhaust port, formed in an outer sidewall thereof with a plurality of elongate grooves aligned lengthwise along the water turbine rear case, and formed in a sidewall thereof with a through hole communicated with the elongate holes,
wherein the elongate grooves of the water turbine rear case are engaged with the elongate grooves of the water turbine front case as the water turbine rear case is coupled with water turbine front case so that one inlet path or a water exhaust path is formed in the sidewall.

12. The water pressure driven tooth brush of claim 11, wherein the reduction module comprises:
a rotary disc provided at a front surface thereof with an output shaft, which protrudes forward and is formed at an outer surface thereof with a gear, and provided at a rear surface thereof with a plurality of planet gear shafts arranged around a center of the rotary disc; and
a plurality of planet gears coupled with the planet gear shafts, respectively, and engaged between the internal gear and a driving gear of the water turbine.

13. The water pressure driven tooth brush of claim 11, wherein the tooth brush head comprises:
a pair of rotary tooth brush hairs including a rotating shaft, in which tooth brush hairs are spirally implanted onto an upper portion of the rotating shaft and a lower end of the rotating shaft extends downward;
a rotary support member to rotatably support the upper portion of the rotating shaft where the tooth brush hairs of the pair of the rotary tooth brush hairs are spirally implanted; and
a head body provided at an upper portion thereof with a coupling protrusion to be coupled with the rotary support member and formed at a lower portion thereof with a shaft hole into which a lower end of the rotating shaft of the pair of the rotary tooth brush hairs is inserted,
wherein the rotary support member includes an anti-splash plate to block water splash caused by the pair of the rotary tooth brush hairs.

* * * * *